United States Patent
Ball et al.

(10) Patent No.: US 6,869,449 B2
(45) Date of Patent: Mar. 22, 2005

(54) PROSTHETIC JOINT COMPONENT HAVING MULTIPLE ARCUATE BENDING PORTIONS

(75) Inventors: Robert J. Ball, Winona Lake, IN (US); Bruce Khalili, Briarcliff Manor, NY (US); Arnold-Peter C. Weiss, Barrington, RI (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 10/261,758

(22) Filed: Oct. 1, 2002

(65) Prior Publication Data

US 2003/0069645 A1 Apr. 10, 2003

Related U.S. Application Data

(60) Provisional application No. 60/327,545, filed on Oct. 5, 2001.

(51) Int. Cl.[7] .................................................. A61F 2/42
(52) U.S. Cl. ................ 623/21.15; 623/21.11; 623/23.41
(58) Field of Search ................ 623/21.11, 21.15, 623/21.19; A61F 2/42

(56) References Cited

U.S. PATENT DOCUMENTS

| | | | |
|---|---|---|---|
| 3,462,765 A | | 8/1969 | Swanson |
| 3,593,342 A | | 7/1971 | Kahn et al. |
| 3,739,403 A | | 6/1973 | Nicolle |
| 3,805,302 A | | 4/1974 | Mathys |
| 3,875,594 A | | 4/1975 | Swanson |
| 3,993,342 A | | 11/1976 | Jones et al. |
| 4,204,284 A | * | 5/1980 | Koeneman ............... 623/23.41 |
| 4,871,367 A | | 10/1989 | Christensen et al. |
| 5,011,497 A | * | 4/1991 | Persson et al. .......... 623/23.41 |
| 5,507,823 A | | 4/1996 | Walston et al. |
| 5,522,900 A | | 6/1996 | Hollister |
| 5,549,690 A | | 8/1996 | Hollister et al. |
| 5,824,095 A | | 10/1998 | Di Maio, Jr. et al. |
| 5,984,970 A | | 11/1999 | Bramlet |
| 5,984,971 A | | 11/1999 | Facciolo et al. |

FOREIGN PATENT DOCUMENTS

| | | |
|---|---|---|
| RU | 2026653 | 1/1995 |
| WO | WO 97/40786 | 11/1997 |

OTHER PUBLICATIONS

Wright Medical Technology, Inc. brochure: *Swanson Finger Joint Implant*, © 1998 Wright Medical Technology, Inc. (2 pages).
Avanta Orthopaedics brochure: *SR Hand Implant System* (1 page).
Avanta Orthopaedics brochure: *PIP SR™ Implant System, MCP SR™ Implant System, TMC SR™ Implant System*, © 1997 Avanta Orthopaedics 19–0116 rev. A (1 page).
Avanta Orthopaedics web pages (www.avanta.org/hand.htm): *Products/Hand Surface Replacement. SR™, Hand Implant System* (3 pages).
Avanta Orthopaedics brochure: Preflex, *MCP Finger Joint Implant*, © 2002 Avanta Orthopaedics 19–0122 rev. A. (1 page—double sided).
Avanta Orthopaedics brochure: *Now you Have a Choice in Soft Skeletal Implants*, Avanta Orthopaedics (1 page).
Avanta Orthopaedics brochure: *SR™ MCP and PIP*, © 2002 Avanta Orthopaedics (1 page).
Avanta Orthopaedics brochure: *The Avanta PIP*, © 1996 Avanta Orthopaedics 190104 rev B.

* cited by examiner

Primary Examiner—Thomas Barrett
(74) Attorney, Agent, or Firm—Maginot, Moore & Beck

(57) ABSTRACT

A joint prosthetic component that includes first and second arms, and a joint member interposed therebetween. The joint member is configured to permit flexion motion between the first and second arms, and includes a first concave surface and a second concave surface. The first concave surface has a plurality of arcuate portions defined therein. The first and second concave surfaces are located on opposing sides of the joint member.

19 Claims, 4 Drawing Sheets

PROSTHETIC JOINT COMPONENT HAVING MULTIPLE ARCUATE BENDING PORTIONS

This application claims the benefit of U.S. Provisional Patent Application Ser. No. 60/327,545, filed Oct. 5, 2001.

FIELD OF THE INVENTION

The present invention relates generally to prosthetic joint components, and more particularly, to prosthetic joint components for use in various extremities.

BACKGROUND OF THE INVENTION

Several prosthetic joints have been proposed for various extremity joints, such as the joints in the hands and feet. For example, U.S. Pat. No. 5,984,970 shows prosthetic joints that may be used in both the distal interphalangeal joints and the proximal interphalangeal joint. Among the desirable qualities of such a prosthetic joint is the ability to provide natural flexion motion and durability. The interphalangeal joints ideally permit at least between 70° and 90° of flexion (i.e. bending the finger or toe in the normal direction) and at least a small amount of hyperextension, (i.e. bending of the finger or toe backwards).

Typically, prosthetic extremity joints, particularly interphalangeal or metacarpophalangeal, are used to replace natural joints compromised by degenerative or inflammatory joint disease, dislocation of the joints, or other painful joints having limitation of motions. Adequate bone stock and lack of infection are typically also required.

Prior art proximal interphalangeal joint prosthetics typically employ two intramedullary stems or arms with a pivoting unit located therebetween. In some devices, the entire prosthetic is formed of a single piece of elastomer. The pivoting unit includes a dorsal concavity and in some cases a small palmar concavity. The concavities provide a "weak" spot that encourages the location of the pivoting deformation to the hinge, thereby producing predictable and natural motion. One drawback to many of these devices is that they employ no angle between the opposing stems in their natural position (i.e. without force applied). Such a position is unnatural as the natural "at-rest" posture of the phalanges is not a straight line.

One product, the Avanta PIP offered by Avanta Orthopedics, addresses this drawback by providing a proximal interphalangeal prosthetic that includes stems that are designed to accommodate the crescent shape of the distal and proximal phalanges.

One drawback to many prior art devices, including the Avanta PIP device, is the potential for failure at the pivot or hinge portion of the implant. Such failures require intervention and, as a result, are extremely undesirable. Some devices used for other joints may be larger and thus less prone to failure, but such devices may not be suitable for small joints such as interphalangeal joints.

Accordingly, there is a need for a prosthetic joint component that is less prone to joint failure than existing joint devices. There is a further need for such a prosthetic joint component that is particularly suited to the limitations of the interphalangeal joints.

SUMMARY OF THE INVENTION

The present invention addresses the above needs, as well as others, by providing a joint prosthetic component that includes a joint member having a concavity that includes multiple arcuate portions. When the joint member is flexed, the joint member bends at each of the arcuate portions. As a result, the stresses and forces exerted during bending of the joint prosthetic component will not tend to be concentrated on a single bend spot or bend line. The concavity having multiple arcuate portions is preferably combined with another concavity on the opposite side of the component to ensure smooth, natural motion and structural integrity. Alternatively, the concavity having multiple arcuate portions is preferably combined with a natural bias angle of the joint that conforms with the natural bias of the human joint, thereby decreasing the overall stress on the device. As a result, the joint member is less prone to failure than a prior art joint member that does not employ multiple bend arcs in a concavity or does not include one of the other above-discussed integrity-enhancing structures.

A first embodiment of the present invention is a joint prosthetic component that includes first and second arms, and a joint member interposed therebetween. The joint member is configured to permit flexion motion between the first and second arms, and includes a first concave surface and a second concave surface. The first concave surface has a plurality of arcuate portions defined therein.

A second embodiment of the present invention is a joint prosthetic component that also includes first and second arms and a joint member interposed therebetween. The first arm defines a first longitudinal axis and the second arm defines a second longitudinal axis. The joint member is configured to permit flexion motion between the first and second arms. The joint member includes a first concave surface having a plurality of arcuate portions defined therein. The first longitudinal axis and the second longitudinal axis extending from each other at an angle exceeding 10° when the joint member is in a normally biased position.

The above described features and advantages, as well as others, will become readily apparent to those of ordinary skill in the art by reference to the following detailed description and accompanying drawings.

DETAILED DESCRIPTION

Figure 7:
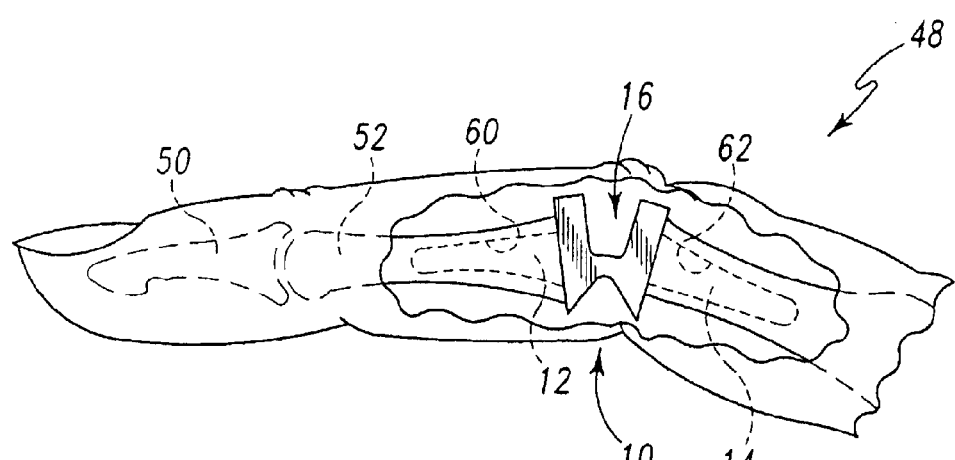
FIG. 7 shows the side view of FIG. 5 with the joint prosthetic component of FIG. 1 implanted to replace the proximal interphalangeal joint.

FIGS. 1 through 4 show different views of an exemplary joint prosthetic component 10 according to the present invention. With reference to those FIGS. 1 through 4, the joint prosthetic component comprises a first arm 12, a second arm 14, and a joint member 16. FIG. 7 also shows the joint component 10 implanted into the proximal interphalangeal (PIP) joint of a human finger 48. The joint prosthetic component 10 is preferably formed of a unitary piece of flexible, biocompatible and tear-resistant elastomer. Various types of suitable elastomers are known, and include without limitation silicon rubber, polyurethane rubber, polycarbonate-based polyurethane, and the like. Those of ordinary skill in the art may readily determine the type and hardness of elastomer used.

In general the first arm 12 and the second arm 14 are configured to be received into intramedullary recesses or bores of adjacent bones. For example, in the exemplary implementation of FIG. 7, the first arm 12 is configured to be received into a bore 60 of the middle phalanges 52 of the finger 48 and the second arm 14 is configured to be received into a bore 62 in the proximal phalanges 54.

Figure 3:
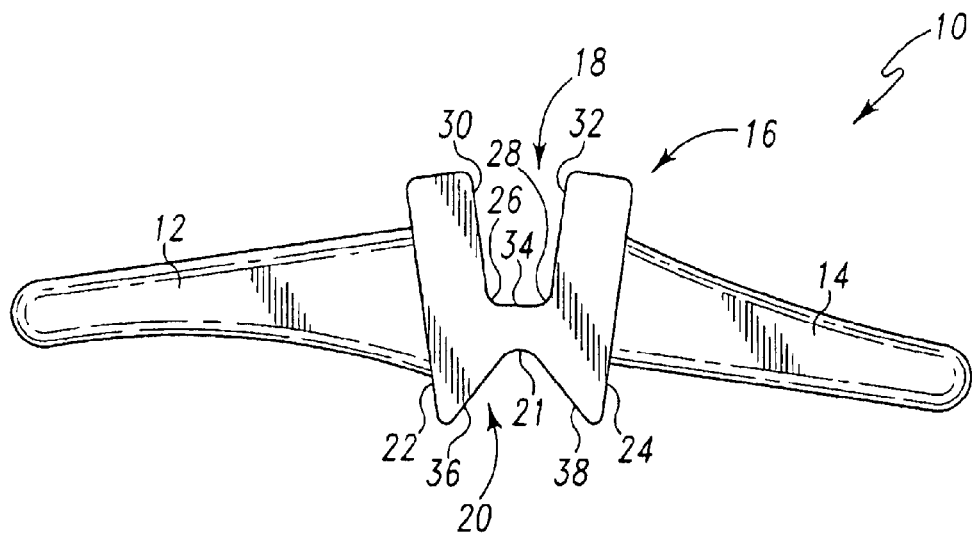
FIG. 3 shows a front plan view of the joint prosthetic component of FIG. 1 in a normally-biased or non-flexion position.
Figure 4:
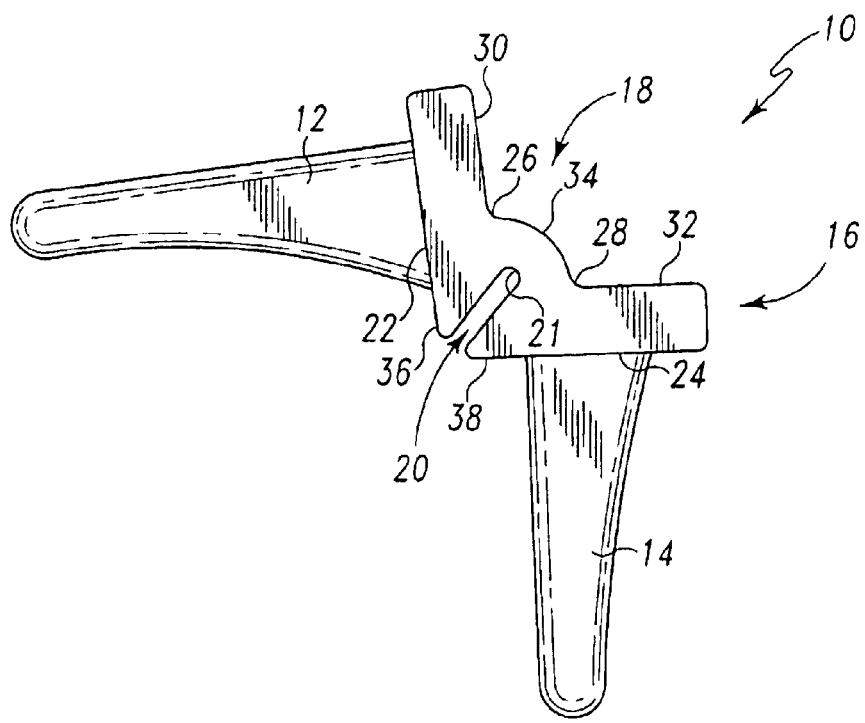
FIG. 4 shows a front plan view of the joint prosthetic component of FIG. 1 in a flexion position.

Referring again generally to FIGS. 1 through 4, the joint member 16 is interposed between the first and second arms 12 and 14, respectively. The joint member 16 is configured to permit flexion motion between the first arm 12 and the second arm 14. Referring specifically to FIGS. 3 and 4, the joint member 16 allows flexion motion between, among other positions, those shown in FIGS. 3 and 4. FIG. 3 shows the prosthetic component 10 in normally biased position, or in other words, an at rest position. FIG. 4 shows the prosthetic component 10 in flexion position.

It will be appreciated that the first arm 12 and second arm 14 in the normally biased position shown in FIG. 3 extend at a slight angle with respect to each other and thus do not form a completely straight line. In particular, the first arm 12 defines an imaginary central axis that extends longitudinally through the center of the first arm 12, and the second arm defines an imaginary central axis that extends longitudinally through the center of the second arm. The central axis of the first arm 12 and the central axis of the second arm 14 are angled with respect to each other when the component 10 is "at rest" or under no significant external force.

The slight angle conforms to the naturally-biased position of the phalanges, which can extend at angles that range from about 10° to 50°, depending on the location of the joint. For example, the natural bias of the PIP joint of the index finger is different than the natural bias of the PIP joint in the ring finger. Those of ordinary skill in the art may readily determine a suitable angle to accommodate the natural bias of any at rest extremity.

It will be appreciated that, in general, flexed position, as used herein, is meant to refer to a flexed position that is the result of purposeful flexion action beyond the angle of the normally-biased joint.

Thus, in accordance with one embodiment of the present invention, the normally biased or non-stressed attitude of the two arms 12, 14 is at an angle that accommodates such natural bias of the joints. As a result, the bias of the prosthetic component 10 will not tend to force the finger in which it is implanted into an unnatural straight position. However, it will be appreciated that at least some of the advantages of the invention relating to multiple arcuate bending portions, discussed further below, may be obtained in a joint prosthetic component that does not employ an pre-angled attitude between the central axes of the arms 12 and 14.

Referring again generally to FIGS. 1 through 4, the joint member 16 includes a first concave surface 18 and a second concave surface 20. The first concave surface 18 has a plurality of arcuate portions 26 and 28 defined therein. In the exemplary embodiment described herein, the first concave surface 18 is located on the dorsal side of the prosthetic component 10, and includes a first side wall 30, a second side wall 32, and a bottom wall 34. The walls 30, 32 and 34 are substantially planar. The first arcuate portion 26 extends medial-laterally and is interposed between the first side wall 30 and the bottom wall 34. The second arcuate portion extends medial-laterally and is interposed between the second side wall 32 and the bottom wall 34.

The arcuate portions 26 and 28 have different radii of curvature. Specifically, although the radial length of the radii of curvature of the arcuate portions 26 and 28 may be substantially identical, the locations of the radii are different. As a result, the arcuate portions 26 and 28 cannot simply be different, non-distinct portions of a single-radius continuous curve. It is preferable that the arcuate portions 26, 28 have radii of curvature that have relatively small radial length. Thus, the two arcuate portions provide multiple weak spots in the joint member 16 at which the bending may occur and at which the stress of bending is concentrated.

The second concave surface 20 is located on the palmar side of the joint member 16 and includes a bending portion in the form of a groove surface 21. The groove surface 21 extends medial-laterally. In a preferred embodiment, the groove surface 21 is located between the first arcuate portion 26 and the second arcuate portion 28 in the proximal-distal plane P (see FIG. 2). Experiments with a device of such preferred construction have shown favorable reduction in stress concentration.

Extending in generally the palmar direction on either side of the groove surface are first and second flanges 36 and 38. The first and second flanges 36 and 38 are configured to engage during flexion movement to inhibit over-flexion. As shown in FIG. 4, during flexion movement, the flanges 36 and 38 travel toward each other.

To this end, the first flange 36 preferably extends in both a palmar and distal direction from the groove surface 21 while the second flange 38 preferably extends in a palmar and proximal direction from the groove surface 21. However, those of ordinary skill in the art may readily determine other flange configurations suitable to limit over-flexion. The flanges 36 and 38, in combination with the groove, also provide a stiffening force that further reinforces the joint member 16, thereby increasing component integrity. The groove surface 21 also inhibits skewed flexion bending.

The joint member 16 includes a first outer surface 22 that intersects with the first arm 12 and a second outer surface 24 that intersects with the second arm 14. The first outer surface 22 extends on one end substantially to the dorsal extreme of the first side wall 30 and extends and defines on the other end the palmar extreme of the first flange 36. Similarly, the second outer surface 24 extends on one end substantially to the dorsal extreme of the second side wall 32 and extends and defines on the other end the palmar extreme of the second flange 38.

Figure 5:
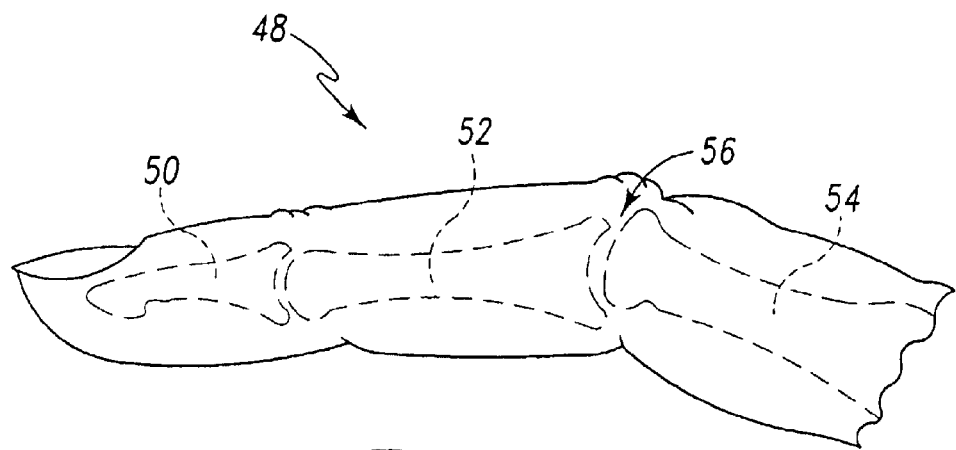
FIG. 5 shows a side view of the phalangeal bones of one finger.
Figure 6:
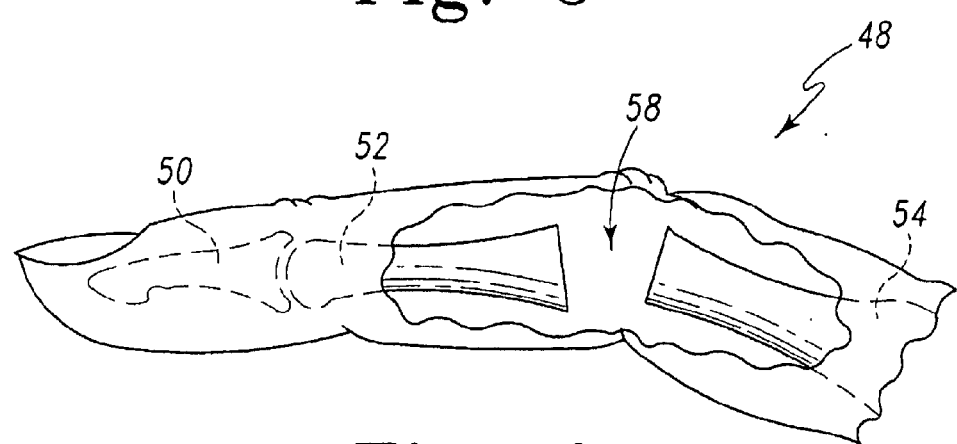
FIG. 6 shows the side view of FIG. 5 with the proximal interphalangeal joint removed.

FIGS. 5, 6 and 7 illustrate the various stages of an implantation method according to the present invention. FIG. 5 shows a finger 48 having, among other things, distal phalanges 50, middle phalanges 52, proximal phalanges 54, and a natural PIP joint 56. Assuming the indications were consistent with implantation of a prosthetic PIP joint, the following method may be implemented.

In general, the incision is made and the site is prepared. To this end, a gradual curving dorsal incision is made over the PIP joint 56. Skin flaps should be gently elevated by careful dissection to expose an appropriate portion of the extensor tendon mechanism, not shown, but which is known to those of ordinary skill in the art. An incision may then be made between the central tendon of the extensor tendon mechanism and lateral band, not shown, on one side of the finger 48. In some cases, an incision may need to be made between the central tendon and the lateral band on the other side of the finger 48 as well. The dorsal capsule, also not shown, is then incised, thereby exposing the PIP joint 56.

After a suitable incision and preparation of the site has been accomplished, the surgeon removes the natural PIP joint 56. To this end, while the central tendon is protected using retractors, a micro-oscillating saw is used to resect the proximal phalanges 54 at a position to remove the PIP joint 56. Spurs are removed from the middle phalanges 52 using a rongeur in order to flatten out the end of the middle phalanges 52.

As shown in FIG. 6, removal of the natural PIP joint 56 results in a void 58 having a size predetermined to receive the prosthetic component 10. The surgeon removes a sufficient amount of the surrounding bone structure on the proximal phalanges 54 and the middle phalanges 52 such that the void 58 is large enough to receive the joint member 16 of one or more sizes of prosthetic components.

Thereafter, the surgeon creates a start hole in the exposed intramedullary tissue of the remaining middle phalanges 52 using a reamer or sharp awl. The surgeon thereafter removes the intramedullary tissue to create a bore 60 in the middle phalanges 52 that is configured to receive the first arm 12 of the prosthetic component 10. To this end, the surgeon uses a series of sequentially-sized broaches, with the final size corresponding to the general dimensions of the first arm 12. The surgeon prepares the proximal phalanges 54 in a similar manner.

Thereafter, the surgeon may attempt a trial fit of the prosthetic component 10. The trial fit may be used for additional sizing or shaping of the bores 60 or 62, or to determine whether additional portions of the end of either of the proximal phalanges 54 or middle phalanges 52 should be removed. Alternatively, or in addition, the trial fit may be used to determine if another size of prosthetic component 10 is required. To this end, the trial implant should seat well against the middle phalanges 52 and the proximal phalanges 54 and be relatively stable.

The surgeon inserts a trial component 10 and then attempts performs flexion and extension movement on the finger 48 to determine if the flexion and extension are both of appropriate range. To insert the component, the surgeon inserts the first arm 12 into the bore 60 of the middle phalanges and inserts the second arm 14 into the bore 62 of the proximal phalanges, as shown in FIG. 7.

During the flexion and extension trial, flexion and extension should occur relatively uninhibited over a predetermined range of motion. The acceptable threshold amount of uninhibited range of motion will vary from patient to patient and may be determined by those of ordinary skill in the art.

In any event, once the appropriate prosthetic component 10 is implanted, the surgeon may close the site using techniques well known in the art. In general, the capsule may be sutured if necessary, and the extensor mechanism should be sutured.

In accordance with the present invention, the above method is not limited to use with the exemplary embodiment of the prosthetic device 10 shown in FIGS. 1–4, but rather may be used with any joint prosthetic device that includes a concave surface having multiple arcuate portions at which bending may occur, and which also has an opposing concave surface. The structure joint integrity, as well as natural and predictable movement, results from such a combination. The method may also be used with a joint prosthetic device that includes a concave surface having multiple arcuate portions and a normally biased position wherein the two insertion arms are at an angle with respect to each other. Such a combination blends the advantages of multiple bending portions and natural bias position that reduce strain on the joint member to enhance the structural integrity of the joint member of the component.

Figure 1:
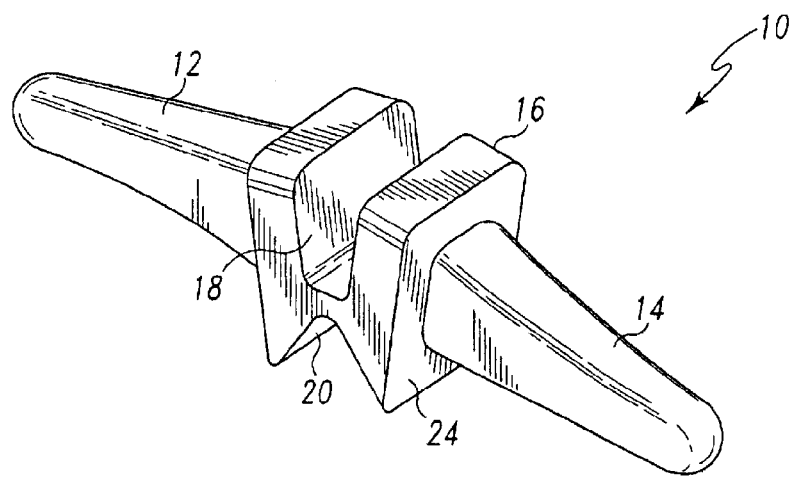
FIG. 1 shows a perspective view of an exemplary embodiment of a joint prosthetic component according to the present invention.
Figure 2:
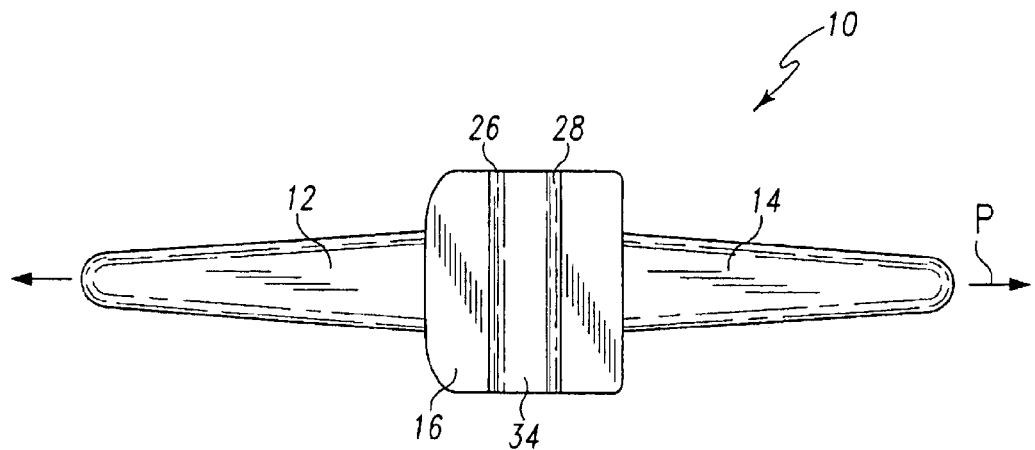
FIG. 2 shows a top (dorsal) plan view of the joint prosthetic component of FIG. 1
Figure 8:
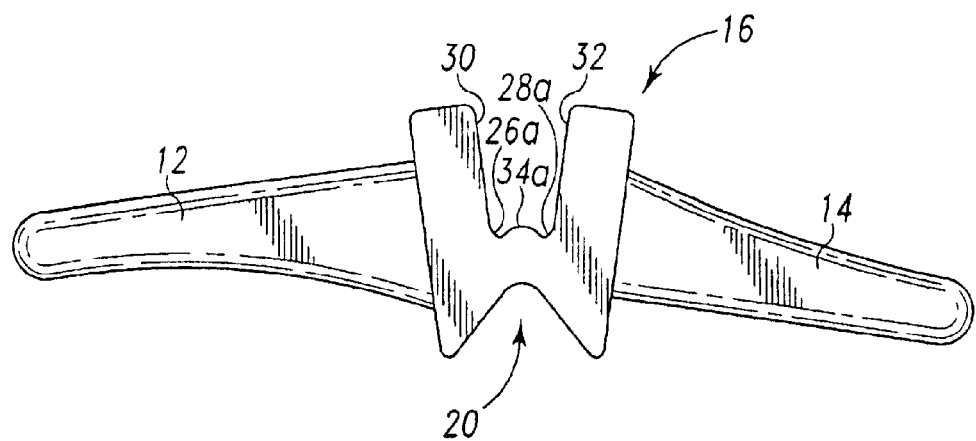
FIG. 8 shows a front plan view of a first alternative embodiment of a joint prosthetic component according to the present invention.

FIG. 8 shows an exemplary alternative embodiment of the prosthetic device 10 of FIG. 1 having a bottom wall 34a that is not planar. Indeed, none of the side walls 30, 32 or bottom wall 34 of FIGS. 1 through 4 need be planar to obtain at least some of the structural integrity advantages of the present invention. FIG. 8 thus illustrates only one example of many alternative embodiments that may be implemented. In FIG. 8, the bottom wall 34a is slightly convex, and sharp, small radius arcuate portions 26a and 28a separate the bottom wall 34a from the side walls 30, 32.

Figure 9:
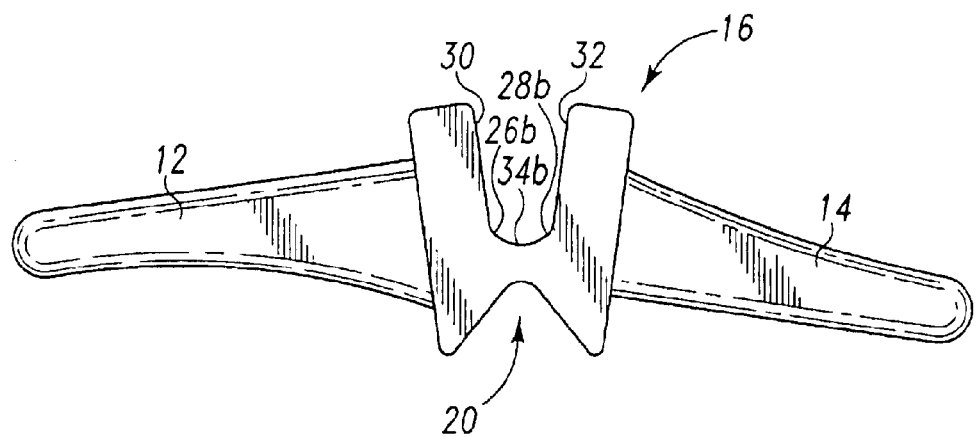
FIG. 9 shows a front plan view of a second alternative embodiment of a joint prosthetic component according to the present invention.

Analogously, FIG. 9 shows another exemplary alternative embodiment of the prosthetic device 10 of FIG. 1 having a bottom wall 34b that is slightly convex. However, in contrast to the prior art, the convex bottom 34b is still bordered by two separate arcuate portions having separately located radii of curvature. Accordingly, as long as the radii of curvature of the two arcuate portions 26b and 28b are significantly smaller than that of the convex bottom 34b, the arcuate portions 26b and 28b will still serve as the natural bending lines of the prosthetic device 10.

It will be appreciated that the above described embodiments are merely illustrative, and that those of ordinary skill in the art may readily devise their own implementations and adaptations that incorporate the principles of the present invention and fall within the spirit and scope thereof. For example, the adaptations that incorporate the geometric structural features described herein may be adapted for use in other interphalangeal joints, or even metacarpophalangeal or metatarsophalangeal joints.

We claim:

1. A joint prosthetic component comprising:
   a proximal arm and a distal arm; and
   a joint member interposed between the proximal arm and the distal arm, the joint member configured to permit flexion motion between the proximal arm and the distal arm, the joint member including a concave dorsal surface and a concave palmar surface,
   wherein the concave dorsal surface has a proximal arcuate portion and a distal arcuate portion defined therein,
   wherein the concave dorsal surface further has a planar bottom wall interposed between and connecting the proximal arcuate portion and the distal arcuate portion,
   wherein the concave palmar surface has only a single arcuate portion, and
   wherein the single arcuate portion of the concave palmar surface is positioned between the proximal arcuate portion and the distal arcuate portion of the concave dorsal surface in the proximal-distal plane.

2. The joint prosthetic component of claim 1, wherein the proximal arcuate portion and the distal arcuate portion have separately located radii of curvature.

3. The joint prosthetic component of claim 1, wherein:
   said concave dorsal surface further includes a proximal side wall and a distal sidewall, the proximal arcuate portion is interposed between the proximal side wall and the planar bottom wall, and the distal arcuate portion is interposed between the distal side wall and the planar bottom wall.

4. The joint prosthetic component of claim 3, wherein the proximal side wall and the distal side wall are relatively planar.

5. The joint prosthetic component of claim 1 wherein:

the proximal arm defines a first longitudinal axis;

the distal arm defines a second longitudinal axis; and the first longitudinal axis and the second longitudinal axis extend from each other at an angle exceeding 10° from each other when the joint member is in a normally biased position.

6. The joint prosthetic component of claim 1, wherein the palmar concave surface includes first and second opposing flanges.

7. The joint prosthetic component of claim 1, wherein:

said single arcuate portion of said concave palmar surface possesses an apex, and said apex is located between the proximal arcuate portion and the distal arcuate portion of the concave dorsal surface in the proximal-distal plane.

8. The joint prosthetic component of claim 1, wherein the entire single arcuate portion of the concave palmar surface is completely positioned between the proximal arcuate portion and the distal arcuate portion of the concave dorsal surface in the proximal-distal plane.

9. A joint prosthetic component comprising:

a proximal arm defining a first longitudinal axis;

a distal arm defining a second longitudinal axis, a joint member interposed between the proximal and distal arms, the joint member including (i) a concave dorsal surface having only a proximal arcuate portion and a distal arcuate portion defined therein, and (ii) a concave palmar surface having only a single arcuate portion defined therein;

wherein the first longitudinal axis and the second longitudinal axis extending from each other at an angle exceeding 10° when the joint member is in a normally biased position wherein the concave dorsal surface further has a planar bottom wall connecting the proximal arcuate portion and the distal arcuate portion, and wherein the single arcuate portion of the concave palmar surface is positioned between the proximal arcuate portion and the distal arcuate portion of the concave dorsal surface in the proximal-distal plane.

10. The joint prosthetic component of claim 9, wherein the proximal arcuate portion and the distal arcuate portion have separately located radii of curvature.

11. The joint prosthetic component of claim 10, wherein:

said concave dorsal surface further includes a proximal side wall and a distal sidewall, the proximal arcuate portion is interposed between the proximal side wall and the planar bottom wall, and the distal arcuate portion is interposed between the distal side wall and the planar bottom wall.

12. The joint prosthetic component of claim 11, wherein the proximal side wall and the distal side wall are relatively planar.

13. The joint prosthetic component of claim 11, wherein the concave palmar surface includes first and second opposing flanges.

14. The joint prosthetic component of claim 9, wherein:

said single arcuate portion of said concave palmar surface possesses an apex, and said apex is located between the proximal arcuate portion and the distal arcuate portion of the concave dorsal surface in the proximal-distal plane.

15. The joint prosthetic component of claim 9, wherein the entire single arcuate portion of the concave palmar surface is completely positioned between the proximal arcuate portion and the distal arcuate portion of the concave dorsal surface in the proximal-distal plane.

16. A method of implanting a joint prosthetic device comprising:

a) removing a portion of a first phalangeal bone, a second bone, including a natural joint between said first phalangeal bone and said second bone;

b) implanting a prosthetic component between a remaining portion of the first phalangeal bone and a remaining portion of the second bone, the prosthetic component including:

a proximal arm and a distal arm; and a joint member interposed between the proximal arm and the distal arm, the joint member configured to permit flexion motion between the proximal arm and the distal arm, the joint member including a concave dorsal surface and a concave palmar surface, wherein the concave dorsal surface has a proximal arcuate portion and a distal arcuate portion defined therein, wherein the concave dorsal surface further has a planar bottom wall interposed between and connecting the proximal arcuate portion and the distal arcuate portion, wherein the concave palmar surface has only a single arcuate portion, and wherein the single arcuate portion of the concave palmar surface is positioned between the proximal arcuate portion and the distal arcuate portion of the concave dorsal surface in the proximal-distal plane.

17. The method of claim 16 further comprising, after step a) removing intermedullary bone tissue from the first phalangeal bone to create a bore for receiving the first arm of the prosthetic component.

18. The method of claim 16 wherein step a) further comprises removing a portion of the second bone, the second bone comprising a second phalangeal bone.

19. The method of claim 16, further comprising performing flexion and extension movement on the implanted prosthetic component and removing the implanted prosthetic component if the flexion and extension movement is inhibited within a test range of motion.

* * * * *